United States Patent
Bertaud et al.

(10) Patent No.: US 10,772,811 B2
(45) Date of Patent: Sep. 15, 2020

(54) AQUEOUS IONIC SOLUTION, MADE FROM DISSOLVED MINERAL SALTS, IN PARTICULAR INTENDED FOR THROAT CARE

(71) Applicant: LABORATOIRE DE LA MER, Saint-Malo (FR)

(72) Inventors: Olivier Bertaud, Saint-Malo (FR); Anne Beaulieu, Saint-Malo (FR); Ludovic Mimot, Saint-Malo (FR)

(73) Assignee: LABORATOIRE DE LA MER, Saint-Malo (FR)

( * ) Notice: Subject to any disclaimer, the term of this patent is extended or adjusted under 35 U.S.C. 154(b) by 26 days.

(21) Appl. No.: 15/563,131

(22) PCT Filed: Mar. 8, 2016

(86) PCT No.: PCT/EP2016/054935
§ 371 (c)(1),
(2) Date: Sep. 29, 2017

(87) PCT Pub. No.: WO2016/155992
PCT Pub. Date: Oct. 6, 2016

(65) Prior Publication Data
US 2018/0071184 A1 Mar. 15, 2018

(30) Foreign Application Priority Data
Apr. 2, 2015 (FR) ...................... 15 52862

(51) Int. Cl.
| | |
|---|---|
| A61K 8/34 | (2006.01) |
| A61Q 11/00 | (2006.01) |
| A61P 11/02 | (2006.01) |
| A61K 8/60 | (2006.01) |
| A61K 8/96 | (2006.01) |
| A61K 8/98 | (2006.01) |
| A61K 35/08 | (2015.01) |
| A61K 47/10 | (2017.01) |
| A61K 9/00 | (2006.01) |
| A61K 9/10 | (2006.01) |
| A61K 9/107 | (2006.01) |
| A61K 36/45 | (2006.01) |
| A61K 45/06 | (2006.01) |

(52) U.S. Cl.
CPC ............ *A61K 8/345* (2013.01); *A61K 8/60* (2013.01); *A61K 8/965* (2013.01); *A61K 8/988* (2013.01); *A61K 9/006* (2013.01); *A61K 9/10* (2013.01); *A61K 9/1075* (2013.01); *A61K 35/08* (2013.01); *A61K 36/45* (2013.01); *A61K 45/06* (2013.01); *A61K 47/10* (2013.01); *A61Q 11/00* (2013.01); *A61K 9/0095* (2013.01); *A61K 2800/92* (2013.01)

(58) Field of Classification Search
CPC .................................. A61K 8/60; A61K 35/08
See application file for complete search history.

(56) References Cited

U.S. PATENT DOCUMENTS

| | | | | |
|---|---|---|---|---|
| 5,284,833 A | * | 2/1994 | McAnalley | A61K 45/06 424/543 |
| 5,922,324 A | | 7/1999 | Aga et al. | |
| 2015/0104527 A1 | | 4/2015 | Andro et al. | |

FOREIGN PATENT DOCUMENTS

| | | | | |
|---|---|---|---|---|
| EP | 2068896 B1 | 3/2017 | | |
| FR | 2 971 713 A1 | 8/2012 | | |
| WO | WO-2012110665 A1 | * | 8/2012 | ............ A61K 9/0043 |

OTHER PUBLICATIONS

Apr. 25, 2016 Search Report issued in International Patent Application No. PCT/EP2016/054935.

\* cited by examiner

*Primary Examiner* — Kyle A Purdy
(74) *Attorney, Agent, or Firm* — Oliff PLC; R. Brian Drozd

(57) ABSTRACT

An aqueous ionic solution based on dissolved mineral salts, in particular intended for throat care, especially for the treatment, prevention and relief of manifestations related to sore throats. The aqueous ionic solution includes: by way of aqueous solvent, at least 20% by weight, with respect to the total weight of the composition, of a hypertonic solution of mineral salts having an osmolality greater than 350 mOsm/kg; at least 50% of one or more polyols of plant origin, by weight with respect to the total weight of the ionic solution; at least one sucrose and C8-C24 fatty acid ester, by weight with respect to the total weight of the ionic solution; and a non-alcoholic extract of propolis and/or between 1% and 8% honey, by weight with respect to the total weight of the ionic solution.

19 Claims, No Drawings

AQUEOUS IONIC SOLUTION, MADE FROM DISSOLVED MINERAL SALTS, IN PARTICULAR INTENDED FOR THROAT CARE

The present invention relates to an aqueous ionic solution, made from dissolved mineral salts, in particular intended for throat care, especially for the treatment, prevention and relief of conditions related to sore throats.

Sore throats are a symptom with many origins, infectious and non-infectious. Sore throats of non-infectious origin are related to contact of the mucosa or the ear, nose and throat sphere with irritating subjects such as tobacco, alcohol, pollution or allergens. Sore throats of infectious origin result from the exposure of the mucosa of the ear, nose and throat sphere to viruses or bacteria.

Pharyngitis is one of the pathologies of infectious origin associated with sore throats. This is an inflammation of the pharynx. It is the most common ear, nose and throat ailment that affects the whole of the population, from the smallest to the oldest. It has local signs little different from tonsillitis, in particular sore throat, fever and difficulties in swallowing. Pharyngitis is often associated with a cold. It may also be accompanied by acute otitis, acute sinusitis and/or acute bronchitis. It is usually of viral origin. In children, it develops mainly in the upper part of the pharynx, the rhinopharynx. Acute rhinopharyngitis is the most common illness in children.

Tonsillitis is an inflammation, of infectious origin, of the tonsils, or even of the whole of the oropharynx, which become red and swollen, sometimes covered with white or yellowish spots. It manifests itself at the beginning with prickling felt in the throat, a more or less great problem with swallowing, or even painful swallowing, a sensation of burning in the throat, a tendency to cough and to clear ones throat when mucus forms, sometimes a cough and pain irradiating as far as the ears. In 80% of cases, tonsillitis is of viral origin and benign. It is a frequent and commonplace illness. Only 30% of cases of tonsillitis are of bacterial origin and must benefit from antibiotic treatment. Bacterial tonsillitis has a frequency peak in children at between 5 and 15 years. It is rarer in children of less than 3 years as well as in adults.

The main infectious agents involved in infections of the ear, nose and throat sphere, such as pharyngitis and tonsillitis, are viruses in 40% of cases and bacteria in 30% of cases. Concerning viruses, it is a case mainly of rhinovirus, adenovirus, syncytial respiratory virus, or influenza A and B. It may also be a case of the herpes virus with a lower incidence, but more severe episodes in terms of symptoms.

Concerning bacteria, it is a case mainly of β-haemolytic streptococci bacteria of group A (GABHS, also referred to as *S. pyogenes*) and more rarely *S. viridans, M. pneumoniae, C. pneumoniae* or *H. influenza*.

It should be noted that, in 30% of cases, the infectious origin is not known or identified.

Untreated, tonsillitis and pharyngitis may be the source of local peripharyngeal complications: bacterial secondary infection, amygdalitis or peritonsillar phlegmon, for example.

The treatment of these pathologies, such as pharyngitis and tonsillitis of viral origin, is symptomatic. Only streptococcic infections are treated with antibiotics. Sampling followed by a rapid test is carried out at a general practitioner in order to determine the nature of the treatment.

With regard to the active principles used at the present time, the majority of medicinal preparations most frequently used contain:
- an antiseptic alone, such as hexamidine, acetarsol sodium, chlorhexidine, hexitidine, benzylkonium chloride, etc,
- an antiseptic associated with an anaesthetic, such as tetracaine, lidocaine, butoform, etc,
- an anti-inflammatory, such as lysozyme, alpha-amylase, papaine, ribonuclease, etc.

Treatments of sore throats using such compounds have many drawbacks:

Local antiseptics have no effect on pharyngeal pain, do not exhibit any emollient action, and are subject to limited dosage and duration of use. Repeated use of antiseptic may cause an imbalance in the commensal flora of the buccopharyngeal cavity that fulfil an essential role in the control of infections and the immune system. Antiseptics do not target a single pathogen but weaken the whole of the resident flora. Local antiseptics prolong the duration of reformation of a "healthy" biofilm, which would participate in the protection of the mucosa, exposing convalescent subjects to a risk of recurrence.

Local anaesthetics associated with local antiseptics may prove to be dangerous to the throat, where they are liable to cause "false routes" during food-related swallowing, through anaesthesia of the oropharyngeal junction. They must be used at a distance from meals and drinks. They are in particular inadvisable in children of less than 12 years and aged persons. The dose and duration of use are limited. Furthermore, they prevent correct functioning of the mucociliary blanket by blocking the movement of the cilia. They allow the infected mucus to stagnate on the surface of the mucosa, amplifying the inflammatory phenomenon. They unbalance the normal microbial flora of the mouth with a risk of bacterial or fungal diffusion. Repeated or prolonged treatment at the mucosa may expose to risks of toxic systemic effects of the contact anaesthetics (attack on the central nervous system with convulsions, depression of the cardiovascular system). The attention of sportspersons will be drawn to the fact that this speciality contains an active principle, the local anaesthetic, which may cause a positive reaction to tests carried out during anti-doping checks.

Anti-inflammatories do not have any antiseptic action, have no effect on the pain and have no advantage in the case of infection of viral origin. Their action is produced on the pharyngeal oedema. There also, the dose and duration of use are limited.

With regard to products of natural origin, some products proposed are produced from compounds coming from plants or beehive products: extracts of green tea, chamomile, scots pine, honey, essential oils or concentrate of lemon. The herbal-medicine products offered at the present time have an essentially soothing action, lack instantaneous efficacy and/or efficacy on the pain over the long term.

With regard to galenic forms, the majority of medicinal or herbal-remedy preparations used are in the form of lozenges and sprays. Approximately 60% of the French population declared that they use lozenges for easing sore throats and approximately 40% sprays.

The galenic form of such a product for the throat is an important characteristic, related to the efficacy of the product. This is because the use of lozenges in young children and old people is not suitable and inadvisable. With regard to the liquid formulations suitable for being delivered in a spray, the solutions must be maintained in a form that is stable over time, without phase separation or precipitation, and without microbial contamination. A major difficulty stems from the fact that some liquid compositions, for example in the aqueous phase, include lipophilic active compounds. To allow affinity and solubility of components with each other, it is necessary to add adjuvants, such as emulsifiers or surfactants. Some products thus contain such adjuvants, often of non-natural origin, with an allergenic or irritant character. Such compounds are also liable to modify the taste of the product, making it unsuitable for treatment over a long period. The selection thereof when formulating a product intended to be ingested orally and put in contact with the mucosa is particularly tricky.

Moreover, compositions formulated from aqueous phases are liable to contamination by microorganisms. Microbial contamination may occur during manufacture or packaging (primary contamination) or during storage and use of the compositions (secondary contamination). They must therefore contain one or more preservatives. Such preservatives are often derived from the chemical industry, which is not desirable when a natural product is envisaged. In addition, some preservatives are liable to have undesirable effects when the concentration thereof is too great, such as allergic reactions or other forms of intolerance. The development of formulations free from such compounds would thus be entirely advantageous.

The three main criteria of choice with users of products for sore throats are as follows: immediate action, efficacy for treating and easing the sore throat and prolonged action over a long period. The intention to have available non-toxic natural solutions in the long term is added to that. In addition, such products must necessarily be stable over time, and easy to use, at any time of the day, in children, even very young ones, and adults.

The applicant company has taken an interest in saline ionic solutions in the treatment of sore throats. Hypertonic solutions based on sea water, such as those described in the European patent application EP 2 068 896 A1 belonging to the applicant company have decongestant properties for the mucosa that are advantageous in the context of throat care. Applied to the throat mucosa, they make it possible to reduce pharyngeal oedema by osmotic action, to fluidify excess mucosa and to discharge pathogens and inflammation mediators by mechanical action. Thus the discharge of pathogens and mucus is achieved here by fluidification and deglutition. However, there is not really any antiseptic or antiviral activity strictly speaking. In addition, they do not have any immediate effective action against pain. Furthermore, such hypertonic solutions have a viscosity close to that of pure water and prove to be too liquid to effectively adhere to the mucosa for a significant action time.

The objective of the present invention is to overcome all the drawbacks presented in relation to the aforementioned products.

In particular, the aim of the present invention is to propose an aqueous ionic solution produced from compounds of natural origin, which is effective in the treatment or prevention of sore throat and manifestations thereof, in particular of infectious origin, which is stable over time without giving rise to phenomena of phase separation or precipitation despite the incorporation of compounds that are not miscible with an aqueous phase, which is effective against primary or secondary contaminations, which can be used in both adults and young children, without having a taste unfavourable to ingestion, without modifying the breath unfavourably, which is able to be delivered in a spray or the like, which shows itself to be effective against pain rapidly, both immediately and over the long term, which adheres to the mucosa without giving rise to sensations of suffocation or false routes or any interference with swallowing, which can be used several times a day, for example at least six times a day, and which does not give rise to any negative consequences for general health because of its composition.

Another aim of the present invention is to propose such an aqueous ionic solution that is termed multi-action, that is to say which treats a plurality of known manifestations of sore throat at the same time, in particular pain, inflammation, the presence of bacterial or viral sources, difficult swallowing, the sensation of burning and irritation and hoarseness, and coughs. In particular, anti-inflammatory action, antiseptic action, osmotic action, mucolytic and fluidifying action and emollient, calming and soothing action will be sought.

To this end, the invention relates to an aqueous anionic solution, in particular intended for throat care, comprising:
  by way of aqueous solvent, at least 20% by weight, with respect to the total weight of the composition, of a hypertonic solution of mineral salts having an osmolality greater than 350 mOsm/kg,
  at least 50% of one or more polyols of plant origin, by weight with respect to the total weight of the composition,
  at least one sucrose and C8-C24 fatty acid ester,
  an extract of propolis and/or honey.

Advantageously, the aqueous ionic solution comprises between 30% and 40%, more preferentially between 30% and 35%, by weight with respect to the total weight of the composition, of said hypertonic solution of mineral salts having an osmolality greater than 350 mOsm/kg.

A hypertonic solution is a saline solution with an osmolality higher than that of blood, and therefore greater than 300 mOsm/kg, approximately. Such a solution exerts an osmotic pressure higher than that of normal blood plasma. For example, a solution of sodium chloride (NaCl) the concentration of which is greater than 9 g/l is a hypertonic solution.

The hypertonic solution of mineral salts used as the aqueous solvent in the context of the present invention is chosen from the group consisting of pure seawater, dilute seawater and aqueous solutions containing salts, in particular sodium chloride, and further comprising optionally at least one other salt chosen from those naturally contained in seawater. In this regard mention will be made, apart from sodium chloride, of magnesium chloride, magnesium sulfate, calcium sulfate, potassium sulfate, calcium carbonate and magnesium bromide. The composition of seawater is indicated in the Handbook of Chemistry and Physics $63^{rd}$ edition, 1982-1983, page F 163, CRC PRESS.

Advantageously, the hypertonic solution of mineral salts is a solution containing between 22 and 25 g/l, preferentially between 22 and 23 g/l, of dissolved mineral salts of sodium, chlorine, sulfate, magnesium, calcium and potassium.

In a preferred embodiment of the invention, the hypertonic solution of mineral salts is based on seawater, and has:
  an osmolality greater than 350 mOsm/kg, preferably between 500 and 2000 mOsm/kg, preferably between 550 and 700 mOsm/kg, and more preferentially still between 600 and 650 mOsm/kg,
  a composition from the ionic point of view that is qualitatively that of seawater and the following concentrations of $Na^+$, $K^+$, $Mg^{2+}$, $Ca^{2+}$, and $Cl^-$:
  for $Na^+$, 5000 to 19,000, preferably 5500 to 8000, and more preferentially still 6000 to 6500 mg/l
  for $K^+$, 50 to 650, preferably 100 to 250 mg/l
  for $Mg^+$, 1000 to 4000, preferably 1000 to 2000, and more preferentially still 1100 to 1500 mg/l
  for $Ca^{2+}$, 300 to 1200, preferably 350 to 450 mg/l for Cl⁻, 8000 to 33,000, preferably 9000 to 15,000, and more preferably still 10,000 to 13,000 mg/l.

Advantageously, such a preferred hypertonic solution also contains bromine (Br), aluminium (Al), fluorine (F), iodine (I), iron (Fe), zinc (Zn), copper (Cu), manganese (Mn) and selenium (Se).

Such a hypertonic solution based on seawater, which will be referred to as the "reference hypertonic solution" in the remainder of the present description, can be obtained by dilution with distilled water. However, particularly advantageously, such a solution is obtained by a method including one or more electrodialysis steps so as to adjust the concentrations of ionic elements. Such a solution and the method for preparing same are already described in the patent application EP 2 068 896 A1.

The solution of hypertonic mineral salts acts in the throat, in particular on the oedema, by osmotic effect, immediately. It also acts effectively to eliminate bacteria and viruses and the inflammation mediators by mechanical action in particular. It fluidifies and lyses the mucus, facilitates elimination of same and promotes mucociliary clearance. It participates in the mechanisms of healing of the mucosa.

The ionic solution also comprises polyols of plant origin in a large quantity. In this regard and preferably, the solution comprises between 50% and 65% said polyol or polyols of plant origin, by weight with respect to the total weight of the composition.

"Plant origin" means a compound coming from a preferentially renewable plant source.

By way of polyols, mention will be made of glycerol, sorbitol, maltitol, mannitol and xylitol.

According to a preferred embodiment, the polyols of plant origin chosen are glycerol to at least 90%, preferably at least 95%, and sorbitol to 5% to 10%, by weight with respect to the total weight of said polyols.

The aqueous ionic solution according to the invention comprises at least 20% seawater, which represents a medium favourable to contamination by microorganisms, such as bacteria, during manufacture of packaging thereof (primary contamination) or during storage and use thereof at the consumer. The quantity of polyols included in the ionic solution reduces the activity of the water and prevents the proliferation of microorganisms while dispensing with the addition of preservatives.

The polyols, in particular glycerol, also act by way of humectant, able to retain moisture at the mucosa to which the solution is intended to be applied. This function participates in the anti-pain action, facilities swallowing, and reduces sensations of burning, prickling and irritation.

Propolis and/or honey have in particular a calming and soothing action at the mucosa. The honey is advantageously acacia honey. The extract of propolis preferentially does not contain any alcohol, which is an irritant for the mucosa.

Advantageously, the solution comprises between 0.5% and 8% non-alcoholic extract of propolis and/or between 1% and 8% honey, by weight with respect to the total weight of the ionic solution.

By way of emulsifiers, the ionic solution according to the invention comprises sucrose and fatty acid esters. These are non-ionic surfactants consisting of a hydrophilic group, sucrose and a lipophilic group, fatty acid. Since sucrose comprises eight hydroxyl functions, it is possible to produce a range of esters from the sucrose monoester to the sucrose octaester. They are non-toxic and non-irritant and have excellent biodegradability.

The sucrose and fatty acid esters suitable in the context of the invention are non-ionic surfactants of plant origin. They have an HLB greater than 10, preferentially between 12 and 15 on the Griffin scale (Griffin W C, Classification of Surface-Active Agents by HLB, Journal of the Society of Cosmetic Chemists 1 (1949): 311). They thus have an effective wetting property and prove to be effective emulsifying agents for solubilising, in the aqueous solvent rich in mineral salts, such as seawater, compounds initially non-miscible in this type of solvent, such as honey or the extract of propolis, or essential oils such as those present in the variants of the invention described hereinafter. It should be noted that selecting surfactants, firstly able to solubilise compounds non-miscible in the aqueous solvent according to the invention and secondly non-irritant and not procuring an unpleasant taste experienced by the user, has proved difficult. By way of comparison, cationic phospholipids of natural origin are not suitable in the context of the present invention since they procure an unacceptable pronounced taste once delivered to the mouth or throat.

Preferentially, the ionic solution according to the invention comprises between 0.01% and 1.00% sucrose and C8-C24 fatty acid ester, by weight with respect to the total weight of the ionic solution.

Preferentially again, the sucrose and fatty acid ester is sucrose laurate. Sucrose laurate has in fact very good wetting efficacy compared with other sucrose and fatty acid esters.

Other sucrose esters are also envisaged, including sucrose caproate, sucrose caprylate, sucrose caprate, sucrose myristate, sucrose palmitate, sucrose stearate or sucrose-coconut fatty acid ester.

The aqueous ionic solution according to the invention is thus in the form a stable emulsion, that is to say a macroscopically homogenous and microscopically heterogeneous mixture of two non-miscible liquid substances, such as oil and water.

According to another feature of the invention, the aqueous ionic solution has a viscosity of at least 15 mPa·s, preferentially between 15 mPa·s and 100 mPa·s. The measurement is carried out in a 400 ml beaker filled with a minimum of 200 ml by a Brookfield RVT apparatus, module 1, speed 10, in direct measurement, at 20° C. and after 1 minute. The viscosity of the solution is greater than that of pure water (1 mPa·s at 20° C.), for reference. It is equivalent to that of a plant oil (approximately 20 mPa·s). Thus the ionic solution according to the invention does not have the characteristics of a gel, that is to say generally a composition gelled by the addition of polymers. In this regard, it is devoid of polymers or gums allowing the establishment of a structure in gel form. Once applied to the throat, it does not procure a choking and annoying effect that can be procured by a gel. Moreover, it remains suitable for being delivered in a spray or atomisation by means of a suitable device, which a gel does not allow optimally.

The ionic solution according to the invention, once delivered in the throat, blankets and adheres to the mucosa. It has a filmogenic character. This characteristic confers on it the property of acting over a long period, both with regard to pain, but also on physiological level. This is because prolonged contact of the solution on the mucosa enables all the components that it contains to exert their actions. By comparison, a solution without viscosity or having a viscosity equivalent to that of pure water would not be able to act at the mucosa except in a transient manner. Such would be the case, for example, with a solution of hypertonic seawater without viscosity having as its main action an action of washing the mucosa. The solution according to the invention therefore constitutes an optimum vehicle for the active compounds intended to act immediately over a longer period, at the mucosa of the throat.

According to one of the preferred embodiments of the invention, the aqueous ionic solution also comprises at least one essential oil, preferentially in a proportion of between 0.001% and 2%, by weight with respect to the total weight of the composition.

Preferentially, the essential oils are chosen from the essential oil of wintergreen (*Gaultheria fragrantissima*), of ravintsara (*Cinnamomum camphora*), of thyme linalool (*Thymus vulgaris L. linaloliferum*), niaouli (*Melaleuca quiquinervia*), rosemary (*Rosmarinus officinalis*), marjoram sylvester (*Thymus mastichina L. cineolifera*) or any essential oil rich in 1,8 cineole compound.

Advantageously, the aqueous ionic solution according to the invention contains essential oil of wintergreen alone or in a mixture with at least one of said essential oils.

Essential oil of wintergreen is generally used in the treatment of arthritic and muscular problems, such as cramps, tendonitis, osteoarthritis and rheumatism. It is an oil composed of methyl salicylate (approximately 99%) and ethyl salicylate (approximately 0.07). It is used here for its analgesic action.

Essential oils of ravintsara, thyme linalool and niaouli are used here for their antiviral and antimicrobial actions. Essential oil of rosemary is used here for its healing and bactericidal action. Essential oil of marjoram sylvester is used here for its expectorant, decongestant and anti-infection action.

Advantageously, the ionic solution comprises any essential oil rich in 1,8 cineole compound. This is because such a compound makes it possible to accelerate ciliary beating, in addition to its antimicrobial properties. The beating of the cilia on the surface of the mucosa is necessary to eliminate pathogen-containing mucus. This action is combined with that of the other components of the solution, in particular with the action of hypertonic solution. This is because the osmotic activity thereof makes it possible to make water leave the mucosa cells and to reduce the viscosity of the mucus in order to eliminate it. At the same time the pathogens are driven from the mucosa by virtue of the essential oils rich in 1,8 cineole compound and are found in solution in the mucus made fluid. They are then eliminated easily with the mucus.

Generally, each essential oil is added at a proportion between 0.001% and 2% by weight with respect to the total weight of the aqueous ionic solution.

Essential oils are insoluble in water. They can be solubilised by means of a high proportion of solubilisers (or surfactants) but which have the drawback of being irritants. In order to prevent this phenomenon while ensuring good dispersion of the essential oils, in a way that is stable over time, the choice of the solubilising compound related, after study, as seen previously, to a sucrose and fatty acid ester. Furthermore, the high concentration of glycerine further improves the dispersion of the essential oils in a saline solution, in particular in seawater, and helps to maintain them in suspension in the final product. The dispersion tests carried out are reproduced in table 1 below.

TABLE 1

| Tests | Stability |
| --- | --- |
| Glycerine + essential oils + hypertonic seawater solution | Unstable - obtaining of an opaque solution, the essential oils are poorly dispersed and rise to the surface |

TABLE 1-continued

| Tests | Stability |
| --- | --- |
| Essential oils + sucrose ester (sucrose laurate) + glycerine + hypertonic seawater | Stable - obtaining of a slightly opalescent solution, the essential oils remain in suspension |

It should be noted that the stability of this dispersion is dependent on the quantity of water added. In the context of the invention, the quantity of saline solution is high, generally between 20% and 40%, in percentage by mass.

According to one embodiment of the invention, the aqueous ionic solution also has a pH of between 4 and 6, preferentially between 4.1 and 5.5, more preferentially between 4.5 and 5.5.

The acidic pH of the solution participates in its antibacterial action. In addition, such a pH participates, with the high polyol content of the solution according to the invention, in the protection thereof against the primary and secondary contaminations explained previously. The majority of microorganisms have their optimum growth pH at around neutrality (pH of 6 to 8). A pH below 4.5-5.0 or greater than 8.0-8.5 can inhibit the multiplication of the majority of bacteria and participate in the protection of the product. Consequently the pH of the solution will preferentially be buffered at approximately 4.5. A test, in accordance with the European Pharmacopeia $7^{th}$ edition 2011 method (ability to reduce the number of bacteria, yeasts and moulds as a function of time, chapter 5.1.3), made it possible to verify the autoprotection of this formula (example to follow).

A pH-regulating agent may be an acid or an acid salt commonly used in the food industry, such as citric acid, citric acid monohydrate or trisodium sodium citrate.

According to a preferred embodiment of the invention, the aqueous ionic solution contains:
  20% to 40% saline solution, preferably undiluted seawater, and a hypertonic solution of mineral salts having as osmolality greater than 350 mOsm/kg, in particular based on pure or diluted seawater,
  at least 50% glycerol,
  between 0.5% and 8% sorbitol,
  between 0.5% and 8% propolis extract,
  between 1% and 8% honey,
  between 0.01% and 1.00% sucrose ester,
  between 0.5% and 8% ethyl alcohol (96%),
  between 0 and 2%, preferentially between 0.001% and 2%, of one or more essential oils of gaultheria, thyme linalool, ravintsara, niaouli, rosemary, marjoram sylvester or any essential oil rich in 1,8 cineole compound,
  between 0.1% and 2% of one or more flavourings,
  between 0.1% and 0.20% pH regulating agent.

The saline solution that can be used is of course as described previously. The flavourings may those commonly used in the food industry, in particular lemon or menthol flavouring. The absence of preservatives is emphasised.

Preferentially, the aqueous ionic solution does not contain any components other than those mentioned above.

Even more preferably, this aqueous ionic solution contains between 0.001% and 0.15% essential oil of gaultheria.

This preferred embodiment of the invention has the advantage of solving all the drawbacks of the products of the prior art and meets all the objectives of the invention.

Table 2 below summarises the main advantages of the aqueous ionic solutions according to the invention in comparison with products of the prior art.

TABLE 2

| Pathology, symptoms, manifestations | Action sought | Antiseptic products | Anaesthetic and antiseptic products | Herbal medicine products | Aqueous ionic solutions according to the invention |
|---|---|---|---|---|---|
| Sore throat, difficult swallowing, dry throat, sensation of burning, coughing, clears his throat | Action of duration | No | Yes | No | Viscous, oily, adherent filmogenic-type galenic form => for prolonged contact and long-duration effect. |
| | Immediate action Emollient action | | | | Hypertonic seawater or hypertonic saline solution formula (at least 20%) => anti-oedema effect Emulsion => emollient, moisturising action |
| Rhinopharyngitis Pharyngitis Tonsillitis of viral origin | Antiviral action Immunostimulant action | Yes | Yes | Yes | Association of oils with antiviral and antibacterial properties, very well tolerated by the mucosa and respiratory channels, rich in 1,8 cineole |
| Risk of secondary infection | Antiseptic action | Yes | Yes | | Acidic pH Essential oils with antiviral and antibacterial properties |
| Sore throat, pain when swallowing (dysphagia) | Pain-relief or analgesic action (without being anaesthetising) Anti-inflammatory action | No | Yes but risk of false route | | Adherent galenic form Essential oil of *Gaultheria fragrantissima* Plant glycerine Neosorb Propolis Honey No risk of false route to oropharyngeal junction (no anaesthetic) |
| Dry throat, sensation of burning | Emollient/calming/soothing action | No | No | Yes | Hone Propolis Adherent galenic form |
| Cough, slight coughing, clearing of throat when mucus is formed | Mucolytic action Anti-catarrh/fluidising for loose cough | No | No | | Hypertonic the saline solution, in particular seawater, by virtue of its richness in minerals, lyses the mucus, promotes mucociliary clearance and participates in the processes of healing and immunity of the mucosa |
| Absence of imbalance of mouth flora, no burning, no disturbance of mucociliary beating. | | | | | No preservatives |

The invention also relates to an aqueous ionic solution as defined previously for use thereof in throat care and the treatment of throat pain, in particular due to a bacterial or viral infection, more particularly due to tonsillitis, pharyngitis, rhinopharyngitis, bronchitis, sinusitis or rhinitis, as well as a method for throat care and treatment of throat pain, in particular due to a bacterial or viral infection, which consists of spraying, in particular in spray form, an aqueous ionic solution as defined previously.

The invention is described hereinafter by means of example embodiments.

Example 1: Aqueous Ionic Solutions for Children (Less than 6 Years) or Adults (More than 6 Years)

Aqueous ionic solutions according to the invention are prepared by means of the ingredients mentioned in table 3. The quantities are expressed as a percentage by mass.

TABLE 3

| Ingredients | Adult solution | Child solution |
|---|---|---|
| Glycerine (glycerol) | Qsp 100 >50 | Qsp 100 >50 |

TABLE 3-continued

| Ingredients | Adult solution | Child solution |
|---|---|---|
| Propolis | 0.5-8.0 | 0.5-8.0 |
| Neosorb 70/70B (Sorbitol) | 0.5-8.0 | 0.5-8.0 |
| Honey | 1.0-8.0 | 1.0-8.0 |
| Menthol | 0.001-0.01 | |
| Ethyl alcohol 96% | 0.5-8.0 | |
| Flavourings | 0.1-2.0 | 0.1-2.0 |
| EO including Gaultheria fragrantissima EO | 0.001-2.000 | |
| Sucrose esters | 0.01-1.00 | 0.05-1.00 |
| Hypertonic seawater | 20.0-40.0 | 25.0-40.0 |
| pH-regulating agent | 0.01-0.20 | |

Preparation of Aqueous Solvent:

A solution based on seawater with a 22 g/l salt content was prepared by electrodialysis, having an osmolality greater 350 mOsm/kg, that is to say a hypertonic solution. The method for producing this seawater-based solution, known from the prior art, is stated below.

Successively: as a raw material, seawater with a salt content greater than 32 g/l is taken, advantageously from a depth of 5 to 10 metres in a zone with strong current movements, for example off Saint-Malo. This water is clarified, filtered and analysed: if the osmolality of the clarified and filtered seawater is higher than the required osmolality, it has soda removed by electrodialysis until the required osmolality is obtained, if the osmolality of the settled seawater is lower than the require osmolality, it is concentrated until the required osmolality is obtained, and then the ionic concentrations of the various ions are adjusted by selective electrodialysis, and the product is filtered and stored under sterile conditions. The ionic concentrations will be adjusted so as to have the characteristics of a "reference hypertonic solution" as described previously.

Preparation of Ionic Solutions:

After each raw material is weighed, the preparations of the ionic solutions are produced in several phases, these phases being able to be different according to the industrial equipment used.

Preparation of Phase A:

Incorporate the glycerine in the mixing vessel.

Successively add the following ingredients under stirring:
 Propolis
 Neosorb 70/70B
 Acacia honey Continue the stirring to complete solubilisation.

Preparation of Phase B:

In a subsidiary vessel, incorporate the 96% ethyl alcohol and the menthol and then mix until the menthol is dissolved. Next introduce the sucrose ester.

Successively add each essential oil and flavouring, taking care to mix thoroughly between each incorporation.

In the context of the child solution, only the flavourings are added to the sucrose ester.

Preparation of Phase C:

Incorporate the hypertonic seawater (22 g/l of salts) in a $2^{nd}$ subsidiary vessel and then add the pH-regulating agent.

Mixing of the Phases:

Under screw stirring, gradually incorporate phase B and phase A. Maintain the stirring.

Gradually add phase C.

Observations:

The solutions are in the form of stable dispersions or emulsions. The results show the presence of micelles (globule of oil) with a mean size of approximately 0.6 µm (diameter). The distribution shows that the smallest micelles have a diameter of around 0.4 µm while the largest a diameter of approximately 1.1 µm (analysis by the dynamic light scattering granulometric distribution method inspired by ISO 22412:2008 on a Malvern Instruments apparatus—ZetaSizer NanoZS).

Example 2: Analysis of Stability vis-à-vis Bacterial Contaminations (in Accordance with the European Pharmacopeia $7^{th}$ Edition 2011 Method) (Tableau 4)

TABLE 4

| Strain tested | Adult solution | Child solution |
| --- | --- | --- |
| Pseudomonas aeruginosa | A | A |
| Staphylococcus aureus | A | A |
| Escherichia coli | A | A |
| Candida albicans | A | A |

TABLE 4-continued

| Strain tested | Adult solution | Child solution |
| --- | --- | --- |
| Aspergillus brasiliensis Classification | A Conformity with criteria A | NC Non-conformity |

A: result conforming to criteria A
B: result conforming to B
NC: result non-conforming The bacteria strains sought are those that are most commonly encountered in production.

The formulae are satisfactory since contamination by *Aspergillus brasiliensis* is acceptable in production. However, the adult solution 1 is more effective against contaminations. Consequently this formulation makes it possible to dispense with filtration steps during the manufacturing method, which represents a saving in time and equipment.

The performance of the adult solution (according to example 1) is explained by the combination of polyols and essential oils in greater quantity, the presence of alcohol and a more acidic pH buffered at 4.1-4.6. The menthol may also have a slight antimicrobial effect.

It should be noted that the formulation for children, free from essential oils and alcohol, is also effective against contaminations because of the quantity of polyols and the acidic pH.

Example 3: Measurement of the Activity of the Water (Aw) (Tableau 5)

TABLE 5

|  | Adult solution | Child solution |
| --- | --- | --- |
| Measurement Aw | 0.664 | 0.676 |

The activity of pure water is 1. The activity of a dehydrated solution is 0. An activity of water less than 0.8 is satisfactory.

The high proportion of polyols in the formula of the adult solution (according to example 1) makes it possible to reduce the activity of the water, which results in auto-protection of the formulae vis-à-vis the development of microorganisms despite a large quantity of aqueous solvent.

Example 4: Flow Velocity Test

Objective:

Measuring the flow velocity of the adult aqueous ionic solution (according to example 1) compared with demineralised water and 22 g/l hypertonic water in order to show a significant difference in viscosity making it possible to demonstrate the adhesion of the solution to a surface, for example to the surface of the throat mucosa.

Equipment Used:
100 ml decanting bulb
Support
Chronometer
Beakers
Scales to $100^{th}$
Operating Method:
Place a beaker on the scales and allow for the tare
Place the bulb on the support and position it above the beaker
Bring the solution to be tested to 20° C. (+/−0.5° C.)

Fill the decanting bulb with the solution to be tested (lower meniscus)

Trigger the chronometer and open the tap of the decanting bulb at the same time

Record the time elapsed and the weight delivered into the beaker.

Results: Tableau 6

TABLE 6

| Product tested | Density | Quantity in g | Quantity in ml | Time elapsed (seconds) | Volume flowrate (ml)/sec |
|---|---|---|---|---|---|
| Demineralised water T°: 20° C. | 1.00 | Test 1 - 139.04 | Test 1 - 139.04 | 21 sec 25 | 6.543 |
|  |  | Test 2 - 138.98 | Test 2 - 138.98 | 21 sec 03 | 6.608 |
|  |  | Test 3 - 138.96 | Test 3 - 138.96 | 21 sec 34 | 6.5117 |
| Mean |  | 138.99 | 138.99 | 21.206 | 6.554 |
| 22 g/l hypertonic water T° 20° C. | 1.008 | Test 1 - 141.45 | Test 1 - 140.33 | 22 sec 63 | 6.201 |
|  |  | Test 2 - 141.21 | Test 2 - 140.09 | 22 sec 46 | 6.237 |
|  |  | Test 3 - 141.44 | Test 3 - 140.32 | 23 sec 84 | 5.885 |
| Mean |  | 141.36 | 140.25 | 22.976 | 6.1076 |
| Adult aqueous ionic solution T°: 20° C. | 1.15 | Test 1 - 160.55 | Test 1 - 139.60 | 36 sec 89 | 3.784 |
|  |  | Test 2 - 160.49 | Test 2 - 139.55 | 36 sec 06 | 3.869 |
|  |  | Test 3 - 160.19 | Test 3 - 139.30 | 36 sec 16 | 3.852 |
| Mean |  | 160.41 | 139.48 | 36.37 | 3.835 |

Conclusions:

An insignificant difference of 0.4464 ml is noted between the demineralised water and the 22 g/l hypertonic seawater. This difference may be related to the difference in temperature and to the salt content (22 g/l hypertonic).

The difference in flow between the references consisting of demineralised water (2.719 ml) or 22 g/l hypertonic water (2.27 ml) and the adult solution according to the invention (according to example 1) is significant, as well as the time elapsed for the bulb to empty. It is also noted that the adult solution adheres slightly to the wall of the decanting bulb, like an oil.

The adult solution according to the invention has viscosity characteristics superior to those of water or a seawater solution, making it suitable for blanketing the mucosa and adhering for a useful time, enabling the active compounds to exert their actions at the mucosa.

Example 5: Flow Velocity Test n° 2

Objective:

Measure the flow velocity of the adult aqueous ionic solution (according to example 1) compared with a solution present on the market and sold under the brand name Pediakid (Laboratoires Ineldea, France) in order to show a significant difference in viscosity, adhesion, flow and coverage making it possible to demonstrate the adhesion and distribution of the solution on the mouth mucosa.

Composition of the Pediakid product: distilled eucalyptus water (*Eucalyptus globulus*), distilled rosemary water (*Rosmarinus officinalis*), seawater based on Dead Sea salt, extract of echinacea (*Echinacea purpurea*), copper, extract of propolis and extract of aloe vera.

Equipment Used
Support plate and bracket
Box
Chronometer
Slide gauge
Rule
3 bottles of adult solution (according to example 1) packaged batch n° 83361
3 Pediakid products with a connecting piece throat spray batch n° 12392

Operating Method

Test 1

Place the plate vertically with an inclination angle of 105° mimicking the passage of the oropharyngeal junction.

Trace 2 lines horizontally spaced apart by 30 cm.

Place 6 points on the top line corresponding to the initial spray point.

Measure, using the bracket and rule, a distance of 10 cm between the position of the bottle and the impact zone on the plate.

At the same time, trigger the chronometer and spray two sprays onto the impact zone.

Record the time elapsed taken by the liquid to reach the bottom line.

Repeat the operation for each product 3 times with cleaning of the plate after each series of 6.

Test 2

Place the plate horizontally.

Trace 1 vertical line on the box in order to delimit a zone for the adult solution (according to example 1), and a zone for the Pediakid solution.

Measure, using the bracket and the rule, a distance of 10 cm between the position of the bottle (mouth connecting piece) and the impact zone on the box.

Spray 1 spray on the zone of the box concerned.

Surround the zone wet by the spray and take the diameter of the circle thus formed.

Repeat the operation for each product.

Results

TABLE 7

| | Test 1 | | | | | |
|---|---|---|---|---|---|---|
| | Test 1 | Test 2 | Test 3 | Mean | Standard deviation | Overall mean |
| Adult solution 1 (in seconds) | 91.47 | 95.88 | 94.23 | 93.86 | 2.23 | 93.58 |
| Adult solution 2 (in seconds) | 96.37 | 118.83 | 102.65 | 105.95 | 11.59 | |
| Adult solution 3 (in seconds) | 80.97 | 82.65 | 79.17 | 80.93 | 1.74 | |
| Pediakid 1 in seconds | 54.77 | 61.83 | 58.45 | 58.35 | 3.53 | 60.54 |
| Pediakid 2 in seconds | 51.72 | 78.43 | 63.12 | 64.42 | 13.40 | |
| Pediakid 3 in seconds | 59.95 | 62.24 | 54.32 | 58.84 | 4.08 | |

The two means can be compared in accordance with the Student test with null Ho as the hypothesis: the flow time of the solution adult and Pediakid products is equivalent.

The hypothesis H1 then becomes: the flow time of the solution adult is longer than that of the Pediakid solution.

$t$ is given by the formula: $t = \dfrac{(m1 - m2)}{ESy}$

With $ES_v$ given by the formula: $\sqrt{\dfrac{S1^2}{n1} + \dfrac{S2^2}{n2}}$

That is to say t=6.78 with $ES_v$=4.87

Referring to the table of the Student t, and taking as an input the value of t thus calculated and as the number of degrees of freedom the value n−1 where n is the number of measurements, that is to say 17 as degrees of freedom, the associated value of p is 2.12 for a of 0.05.

The value of t does not lie in the interval (−2.12:2.12), the hypothesis HO is therefore rejected, and the two products are therefore different in terms of flow time.

TABLE 8

Test 2:

|  | Test 1 | Test 2 | Test 3 | Mean | Standard deviation |
|---|---|---|---|---|---|
| Adult solution (in mm) | 8 9 | 84 | 86 | 86.33 | 2.52 |
| Pediakid (in mm) | 3 5 | 25 | 37 | 32.33 | 6.43 |

The two means can be compared in accordance with the Student test with null Ho as the hypothesis: the spreading of the adult solution of example 1 and that of the Pediakid solution are equivalent.

The hypothesis H1 then becomes: the spread of the adult solution of example 1 is greater than that of the Pediakid solution.

The value of t is calculated using the previous formula: t=13.54

Regarding the table of the Student t, taking into account the input of the value of t thus calculated and the value n−1 as the number of degrees of freedom where n is the number of measurements, that is to say 5 degrees of freedom, the associated value of p is 2.57 for a of 0.05.

The value of t does not lie in the interval (−2.57; 2.57), the HO hypothesis is therefore rejected, and the two products are different in terms of spread.

CONCLUSION

The two tests carried out showed significant differences with regard to flow and dispersion (spread) between the two products.

It is therefore clear from this that, with a better dispersion and a longer flow time, the adult aqueous ionic solution according to the invention can cover a large part of the oropharyngeal mucosa and remain in contact therewith for the time necessary for its action.

The invention claimed is:

1. Aqueous anionic solution, in particular intended for throat care, comprising:
   by way of aqueous solvent, at least 20% by weight, with respect to the total weight of the composition, of a hypertonic solution of mineral salts having an osmolality greater than 350 mOsm/kg,
   at least 50% of one or more polyols of plant origin, by weight with respect to the total weight of the ionic solution,
   between 0.01 and 1.00% of at least one sucrose and C8-C24 fatty acid ester, by weight with respect to the total weight of the ionic solution,
   an extract of propolis and/or honey.

2. The aqueous ionic solution according to claim 1, wherein it comprises between 20% and 40%, by weight with respect to the total weight of the ionic solution, of said hypertonic solution of mineral salts having an osmolality greater than 350 mOsm/kg.

3. The Aqueous ionic solution according to claim 1 or claim 2, wherein the mineral salt solution is a solution based on diluted or non-diluted seawater or a saline solution containing between 22 and 25 g/l, of dissolved mineral salts of sodium, chlorine, sulfate, magnesium, calcium and potassium.

4. The aqueous ionic solution according to claim 1, wherein it comprises between 50% and 65% of said polyol or polyols of plant origin, by weight with respect to the total weight of the ionic solution.

5. The aqueous ionic solution according to claim 1, wherein the polyol or polyols of plant origin are glycerol to at least 90%, by weight with respect to the total weight of said polyols, and the sorbitol to 5% to 10% by weight with respect to the total weight of said polyols.

6. The aqueous ionic solution according to claim 1, wherein it comprises between 0.5% and 8% of said extract of propolis and/or between 1% and 8% honey, by weight with respect to the total weight of the ionic solution.

7. The aqueous ionic solution according to claim 1, wherein it also comprises at least one essential oil, in a proportion of between 0.001% and 2%, by weight with respect to the total weight of the ionic solution.

8. The aqueous ionic solution according to claim 7, wherein the essential oils are chosen from essential oils of gaultheria, ravintsara, thyme linalool, niaouli, rosemary, marjoram sylvester or any essential oil rich in 1,8 cineole compound.

9. The aqueous ionic solution according to claim 8, wherein it contains essential oil of gaultheria alone or in a mixture with at least one of said essential oils.

10. The aqueous ionic solution according to claim 1, wherein it also has a pH of between 4 and 6.

11. The aqueous ionic solution according to claim 1, wherein it has a viscosity at 20° of at least 15 mPa·s.

12. The aqueous ionic solution according to claim 1, wherein it comprises, by weight with respect to the total weight of the ionic solution:
   25% to 40% hypertonic solution of mineral salts having an osmolality greater than 350 mOsm/kg, based on pure or diluted seawater,
   at least 50% glycerol,
   between 0.5% and 8% sorbitol,
   between 0.5% and 8% hydroglycerine extract of propolis,
   between 1.0% and 8.0% honey,
   between 0.01% and 1.00% sucrose and C8-C24 fatty acid ester,
   between 0.5% and 8% ethyl alcohol (96%),
   between 0 and 2%, one or more essential oils of gaultheria, thymus zygis, ravintsara, niaouli, rosemary, marjoram sylvester or any essential oil rich in 1,8 cineole compound,
   between 0.1% and 2% one or more flavourings,
   between 0.1% and 0.2% pH regulating agent.

13. The aqueous ionic solution according to claim 12, wherein it contains between 0.001% and 0.08% of essential oil of *gaultheria*, by weight with respect to the total weight of the ionic solution.

14. A method for throat care and treatment of throat pain which comprises spraying an aqueous ionic solution as defined in claim 1.

15. The aqueous ionic solution according to claim 1, wherein it comprises 32% by weight with respect to the total weight of the ionic solution, of said hypertonic solution of mineral salts having an osmolality greater than 350 mOsm/kg.

16. The aqueous ionic solution according to claim 1, wherein the mineral salt solution is a solution based on diluted or non-diluted seawater or a saline solution containing between 22 and 23 g/l of dissolved mineral salts of sodium, chlorine, sulfate, magnesium, calcium and potassium.

17. The aqueous ionic solution according to claim 1, wherein the polyol or polyols of plant origin are glycerol to at least 95%, by weight with respect to the total weight of said polyols, and the sorbitol to 5% to 10% by weight with respect to the total weight of said polyols.

18. The aqueous ionic solution according to claim 1, wherein it also has a pH of between 4.5 and 5.5.

19. The aqueous ionic solution according to claim 1, wherein it comprises, by weight with respect to the total weight of the ionic solution:
- 25% to 40% hypertonic solution of mineral salts having an osmolality greater than 350 mOsm/kg, based on pure or diluted seawater,
- at least 50% glycerol,
- between 0.5% and 8% sorbitol,
- between 0.5% and 8% hydroglycerine extract of propolis,
- between 1.0% and 8.0% honey,
- between 0.01% and 1.00% sucrose and C8-C24 fatty acid ester,
- between 0.5% and 8% ethyl alcohol (96%),
- between 0.001% and 2%, one or more essential oils of *gaultheria*, thymus zygis, ravintsara, niaouli, rosemary, marjoram sylvester or any essential oil rich in 1,8 cineole compound,
- between 0.1% and 2% one or more flavourings,
- between 0.1% and 0.2% pH regulating agent.

* * * * *